United States Patent [19]

Siderman

[11] Patent Number: 4,865,021
[45] Date of Patent: Sep. 12, 1989

[54] DEVICE FOR HYGIENIZING THE BUCAL CAVITY

[76] Inventor: Miguel A. Siderman, Sarmiento 1462,, 6o-G, 1042 Buenos Aires, Argentina

[21] Appl. No.: 99,008

[22] Filed: Sep. 21, 1987

[30] Foreign Application Priority Data

Sep. 22, 1986 [AR] Argentina ............................. 305,329

[51] Int. Cl.$^4$ ..................... A61C 17/02; A61C 17/032
[52] U.S. Cl. ......................................... 128/66; 433/80; 433/88; 433/96; 604/77
[58] Field of Search ..................... 433/80, 88, 96, 216; 128/66, 62 A; 604/77

[56] References Cited

U.S. PATENT DOCUMENTS

| | | | |
|---|---|---|---|
| 803,474 | 10/1905 | Dennis | 433/80 |
| 1,500,107 | 7/1924 | Chandler | 433/80 |
| 1,646,942 | 10/1927 | Tuorto | 128/66 X |
| 2,238,541 | 4/1941 | Spagnolo | 128/66 X |
| 2,957,476 | 10/1960 | Freeman | 433/88 |
| 3,211,149 | 10/1965 | Fono | 128/62 A |
| 3,379,192 | 4/1968 | Warren | 128/62 A |
| 3,504,666 | 4/1970 | Vireno | 128/66 |
| 3,516,402 | 6/1970 | Toth | 128/66 |
| 3,527,218 | 9/1970 | Westine | 433/80 |
| 3,742,942 | 7/1973 | Westline | 433/80 X |
| 3,847,662 | 11/1974 | Massa | 128/62 A X |
| 4,164,940 | 8/1979 | Quinby | 128/62 A |

FOREIGN PATENT DOCUMENTS 2051582 1/1981 United Kingdom ................. 433/80

*Primary Examiner*—Robert E. Garrett
*Assistant Examiner*—Carl D. Price
*Attorney, Agent, or Firm*—Anthony A. O'Brien

[57] ABSTRACT

A device for irrigating the teeth and bucal tissues comprises a flexible laminar adaptor for placement between the lips and teeth. The adaptor is provided with irrigation nozzles connected to a water supply, and an outlet connected to a drain. The entire mouth is irrigated, as the teeth are not enclosed.

5 Claims, 3 Drawing Sheets

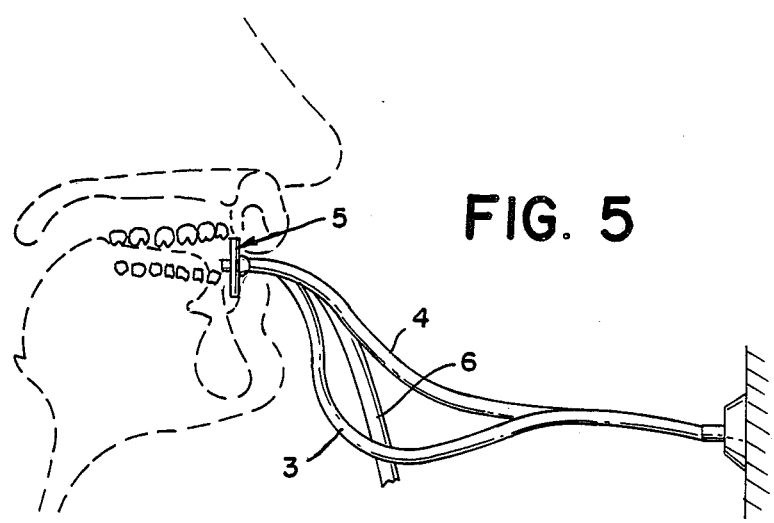
FIG. 5
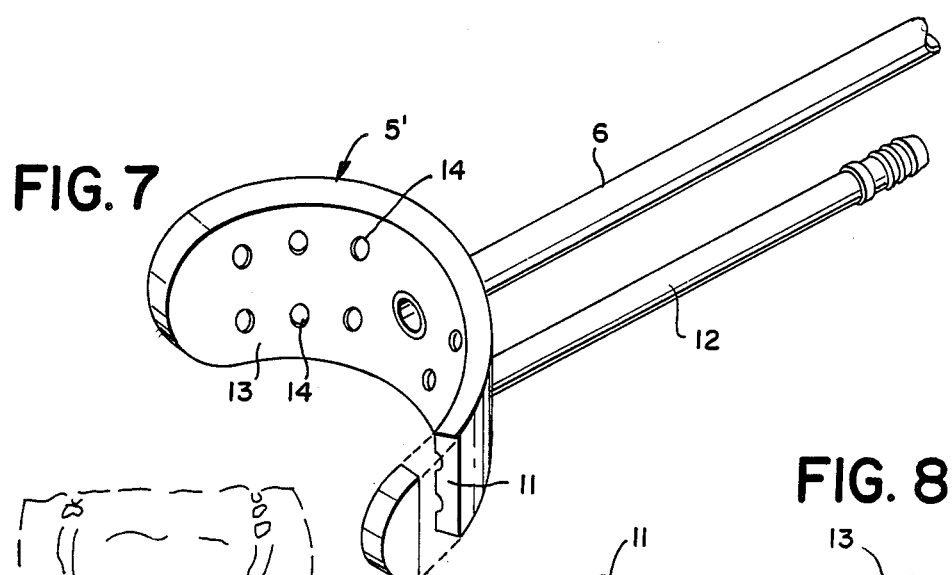
FIG. 7
FIG. 8
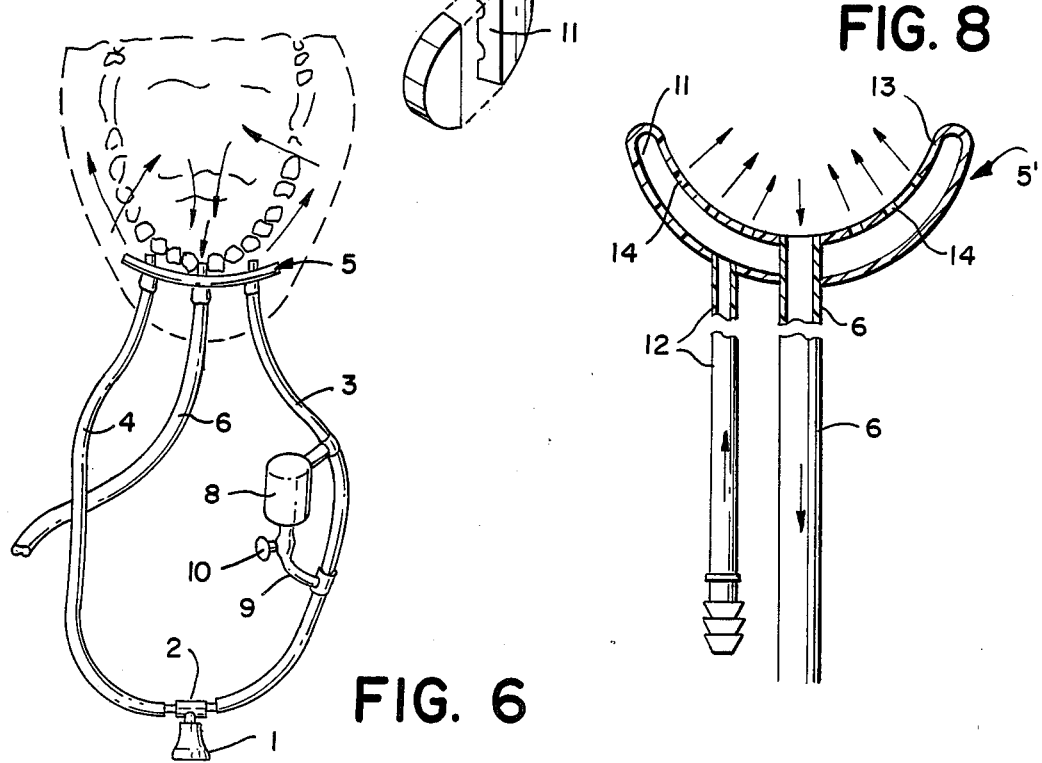
FIG. 6

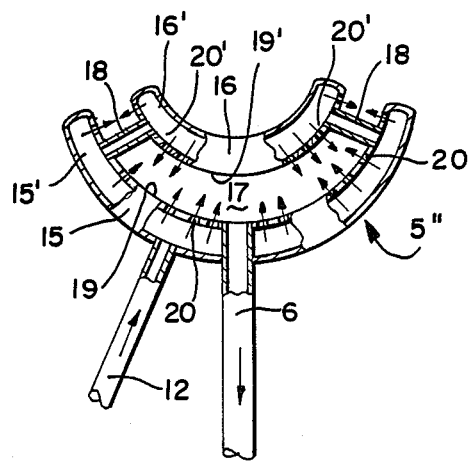
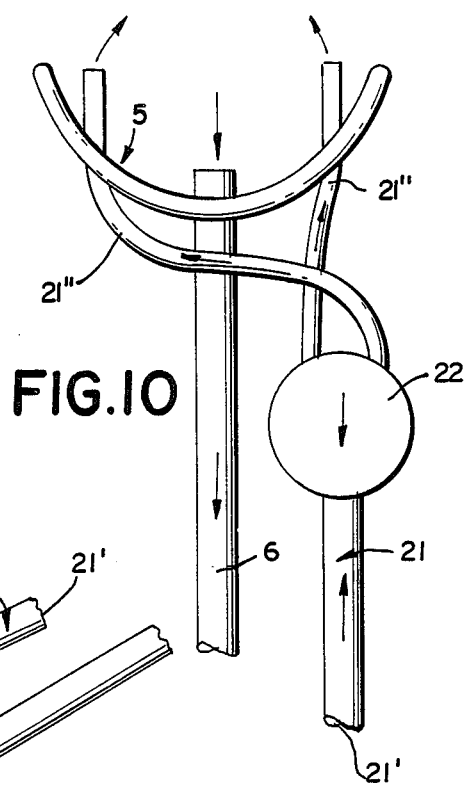
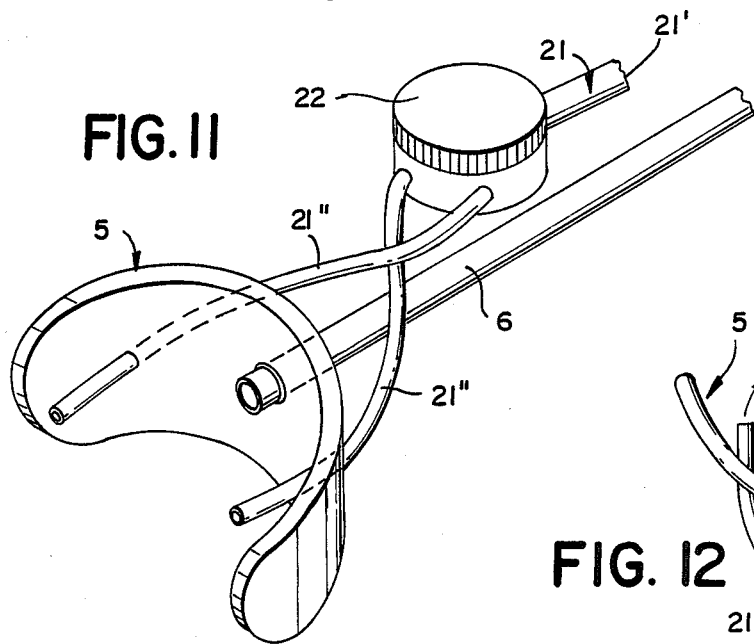
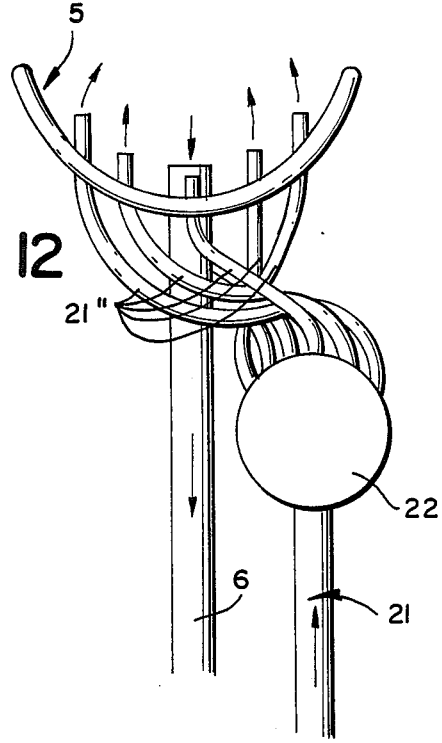
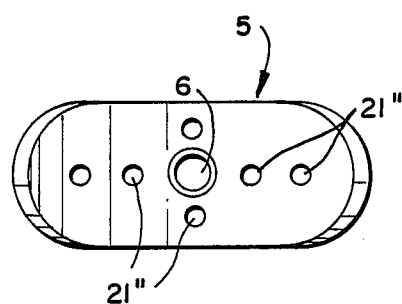

DEVICE FOR HYGIENIZING THE BUCAL CAVITY

BACKGROUND OF THE INVENTION

The present invention refers to a device for hygienizing the bucal cavity, and particularly to a device for preventing the development or ripening of bacterian plaque and eventually to the elimination thereof in order to avoid the inconveniences caused thereby, which are well known.

The device of the invention embodies a number of novel features leading to that purpose and, complementarily, permitting the removal of food residues consequent upon the circulation or continual current of water, selectively orientable by the patient in order thus properly to clean his bucal cavity.

The problems caused by lack of mouth hygiene are known. Such problems are due to the fact that the orcal cavity, being as it is in direct contact with the outside medium, is constantly being attacked by bacteria circulating between the bucal tissues and the saliva.

Up to the present more than 200 types of different bacteria are known and it is also known that there are more bacterial types that have not been isolated.

All this complex bacterian flora circulating in the bucal cavity does not cause any inconveniences until the bacteria are able to form colonies, which reproduce very quickly and increase their number mathematically.

In order that this process may take place it is necessary that the bacteria find a propitious surface they can adhere to and that this surface offer adherence and protection. It is usually represented by the dental surface, which in certain parts offers protection against food particles and the mobile tissues of the mouth.

Under these conditions bacterial plaque is formed. As it develops on the teeth, it is called dental plaque.

This plaque eliminates products of metabolism (residues) which promote gengival inflammation (inflammation of the gums) and constitutes a factor of continuous irritation which in time leads to the destruction of the dental support tissues.

On the other hand, this same plaque metabolizes sugars, transforming them into acids which bring about decalcification of the dental tissues, in other words, caries (necrosis of the teeth).

Although studies made regarding the action of dental plaque on bucal tissues, metabolism, the structure of said plaque, types of bacteria and substances composing same, studies which are progressing constantly, there are still many elements in the system that have not been explained and it is for this reason that no simple means have been found for the removal of said plaque.

In order to hygienize the bucal cavity sundry methods have been applied as well means for the removal of food particles but not for the elimination of dental plaque.

For this purpose toothbrushes of diverse and varied shapes are used as well as toothpicks, dental floss, interdental brushes, water jets and compressed air conveniently directed, etc.

All these mechanisms are localized in this action, i.e., they act upon a given sector of the mouth and must be manipulated or oriented by the patient, directed to sundry sectors to be cleansed and depending on the patient's ability to obtain an improved hygiene.

Inasmuch as the dental arcades have a complex morphology consisting of 32 mutually interrelated parts forming two arcades, the cleansing of all the dental surfaces is very difficult to perform and it is almost impossible to obtain a complete hygienizing with the conventional methods used by the patient and which, in turn, are time consuming and not very practical.

The present invention has for its concrete object a means to control the dental plaque and the use of which means does not imply a great loss of time and does not depend from the patient's ability.

It has been observed that patient who drink water several times a day form fewer dental plaques than those who drink sugar-sweetened beverages. The explanation of this as we know, is that on the one hand the ingestion of sugar favours the formation of plaque and leads to an acid pH thus giving rise to conditions favourable to the development of such plaque.

Water, apart from not containing sugar, would furthermore act as pH modifier, raising the value of said indicator and conditioning the oral medium to diminish the formation of plaque.

In studies made on dental plaque differences have been found between passive plaque and active plaque. The first does not lead to any pathological condition, i.e., it does not affect the tissues and acts as a simple protective film for the dental surface. The second, on the contrary, is the factor giving rise to bucal pathologies.

Under this heading new patterns of oral hygiene can be developed, i.e., that of not giving fundamental immportance to the removal of all the deposits existing on the surface of the teeth but, instead, taking care that said deposits do not develop in such a manner as to become harmful.

The idea of a simple hygiene not calling for any ability on the part of the patient (directed hygiene) and being non-aggressive, i.e., not causing any dental abrasions or retraction of the gums due to trauma produced by hygiene and endeavouring to be as natural as possible, i.e., without any chemical additives, is the fundamental guiding precept of the present invention.

Based on this criterion and in an endeavour to unite all conditions ideal for proper hygiene, an apparatus has been devised embodying a series of features revolutionizing dental hygiene.

SUMMARY OF THE INVENTION

The device of the invention, in order to give substance to the specified objectives, comprises—in a first embodiment a coupling nozzle joined to the outlet of a cold or hot water supply.

Said nozzle is connected to a branch of a tubular "T" coupling, the remaining branches of which are connected to respective conduits the outlets of which are connected to opposite sides of a mouth adaptor consisting of a platelet of flexible material to be inserted and adapted between the lips and teeth of the patient in order to locate both tubes at opposite sides of the mouth and between the upper and lawer jaws.

The adaptor is connected to a central tube to permit drainage of the water after the manner of a drain tube to drain the liquid from the bucal cavity. The end of this adaptor is held between the user's teeth and debouches into a sink.

The diameters of the tubes leading the water into the bucal cavity and draining said water therefrom must be such as to permit a normal and continuous transfer of liquid without any difficulty during the hygienization process, thus avoiding accumulation of water in the patient's mouth.

In a second embodiment the invention comprises a "T" coupling attached to a tube of considerable length and provided with a coupling connecting same to the outlet from the source. The coupling is connected by means of two conduits the ends of which are affixed to the bucal adaptor.

As in the previous case, this latter adaptor comprises a tube to drain the liquid. Said tube reaches up to a sink or receptacle storing the spent liquid.

In a third embodiment, the devices, in at least one of the conduits provided for the entry of water, a tube extending between the coupling and the adaptor itself, a connectiong being provided for dripping a chemical solution, such as disinfecting salts, etc., into the stream of liquid entering the bucal cavity and in this manner completing the hygiene of the mouth.

In a fourth embodiment of the invention, the device is provided without a "T"-coupling and the liquid supply tubes are connected directly to the outlet conduit for the liquid from the supply. In this manner the coupling nozzle is absent from the device.

In this embodiment an especial advantage is obtained in that the device can be used in a consulting room.

In a fifth embodiment of the invention, the device includes a bucal adaptor which is hollow and which limits a chamber in communication, through its outer wall, with at least one water supply conduit passing though said wall. The adapter wall is interiorly arranged in the mouth cavity and is provided with multiple fluid outlet openings communicating said adaptor chamber with the bucal cavity. As in the previous cases, the bucal cavity is communicated with a liquid draining tube passing through the adaptor chamber and its inlet projecting above the inside wall of the latter.

This variational embodiment permits the water to be distributed throughout all the sectors of the dental arcade, depending from the power developed by the jets of water, the diameters and number of openings in the inside wall of the adaptor, etc.

The latter must extend from the left molar vestibulary sector up to the right molar vestibulary sector in order that same may be irrigated over all the external surfaces of the dental pieces crossing the interproximal spaces of the dental arcades.

This variational embodiment offers an excellent distribution of the current of water throughout the entire mouth.

In a sixth embodiment of the invention, the bucal adaptor consists of two similarly shaped pieces of different sizes. These pieces are separated from one another and limit an intermediate space to locate and retain the adaptor by the user's teeth. The adaptor pieces are hollow and define respective chambers connected to one another by a pair of conduits situated in the ends of the space separating both pieces where same are arranged to receive the teeth, in such a manner that both pieces respectively face opposite sides of the dental pieces (vestibulary faces and lingual faces. Both pieces of the adaptor, in their respective walls confronting the dental pieces, comprise a plurality of orifices through which multiple jets of water are projected, said water entering through a supply duct connected to the adaptor piece situated outside the bucal cavity. The interior place of the adaptor is fed through the chamber of the outside piece of the adaptor and the end ducts. The drainage duct in this variant is connected through the outside piece and its outlet is arranged between both pieces of the adaptor.

The purpose of this variational embodiment is to irrigate the internal outer faces (palatine and lingual) and the dental arcades can be located between both pieces, the opposing faces of the teeth receiver simultaneous jets of water.

In a seventh embodiment of the invention, the device contains a liquid inlet duct which is connected between one water supply source and a receptacle the size of which can vary in accordance with requirements. The receptacle is connected to the bucal adaptor by means of a pair of ducts of substantially smaller diameter than the water inlet duct, passing through a pair of ducts and debouching at opposite sides of the bucal cavity.

The purpose of the receptacle is to contain chemical coagents for the treatment of dental pieces. These substances are incorporated into the fluid current entering the receptacle and are transferred to the jets of water entering the bucal cavity.

Such substances can be in a liquid state or in a solid state. In the latter case they are slowly soluble in water and thus can be dosified during the washing operation during a lengthy period of time in accordance with the solubility of the chemical compound used.

The receptacle can furthermore contain salts, abrasive compounds, gel, detergent solutions or any other substance intended to complement the washing operation.

As pointed out above the receptacle in this embodiment is connected by means of two or more conduits to the adaptor and thus it is possible that the washing operation may be a simple one by means of a couple of liquid accesses to the bucal cavity, up to a complex wash in the case that a plurality of agents is used to obtain better distribution of the liquid current.

The receptacle can be connected by means of tubes of small diameter connected to the adaptor and which may be located respectively at opposite sides of the mouth. Also several tubes can be provided to be distributed in the bucal cavity outside the dental pieces, or internally in the bucal cavity beneath the palate.

When increasing the number of conduits inside the bucal cavity not only is a better distribution of water obtained by such an increase but also, by varying the diameter of the tubes, it is possible to increase the power of the fluid jets against the bucal tissues and produce multiple currents with different directions and intensities.

The device of the invention therefore has the object of producing a continuous current of water inside the mouth and commencing in the left and right vestibulary sectors, continuing throughout the entire bucal cavity and leaving through the central region (drainage hose).

This continuous current can modify its original course through action exerted by the user's cheeks or tongue movements, the tongue being furthermore used to regulate the exit of water from the mouth. The time necessary to perform this hygiene is from 1 to 2 minutes.

The water circulates uninterruptedly, passing over all the dental surfaces, including the interdental spaces which are of different access in other hygienizing systems.

This current of water changes direction and velocity continuously following the musclar movements effected by the patient. It also acts on the bacterial plaque by eliminating the bacterial deposits in a sweeping action over the surfaces, without causing a total elimination. It furthermore solubilizes the sugars (carbohydrates) accumulated in the cavity and modifies the pH.

It is convenient to point out that bacterial deposits are not eliminated entirely but that, instead, their maturing is interfered with preventing their reaching a pathological level affecting the bucal tissues.

The invention is an addition to the means available for dental hygiene and, in accordance with the case to be treated, some other complementary element may have to be used.

Consequently, the present invention refers to a hygienizing device for the bucal cavity, particularly for the complementation of odontological treatments, of the kind comprising a liquid supply duct for the supply of cold or hot water, connected to a source of supply of said liquid under normal or raised pressure, and an outlet to be located inside the bucal cavity and oriented against the dental arcades, CHARACTERIZED by the fact of comprising a bucal adaptor to be positioned between the user's lips and dental arcades, said adaptor consisting of at least one plate of flexible material following the contour of said arcades at least partially, the said adaptor being connected to at least one treatment liquid supply duct and said plate presenting at least one pair of outlets for said liquid, connected to said duct and directed towards opposite sides of the bucal cavity in order to generate continuous currents of water between the upper and lower arcades, said plate being crossed by a second liquid drainage duct the inlet of which is situated inside the bucal cavity and the outlet of which debouches into a liquid draining basin.

The invention likeise envisages other accessory objects as will be made clear during the course of the present specification.

BRIEF DESCRIPTION OF THE DRAWINGS

In order that the present invention may be clearly understood and carried into practice same has been illustrated as an example and in one of its preferred embodiments in the attached drawings, in which:

FIG. 5 offers a view of a third embodiment of the device connected directly between the water supply and the bucal cavity of the patient.

FIG. 6 shows a fourth embodiment of the device, incorporating a parallel receptacle containing a disinfecting or medicinal solution which is to be dosified into the current of liquid.

FIGS. 7 and 8 offers plan and perspective views respectively of a fifth embodiment of the device in which a hollow bucal adaptor has been embodied.

FIG. 9 shows a sixth embodiment in which the device uses a double bucal adaptor.

FIGS. 10 and 11, in plan and perspective views, show a seventh embodiment of the invention in which, in the fluid duct inlet a receptacle has been procided which, by means of small-diameter tubes, is connected to the adaptor.

Finally, FIGS. 12 and 13 show an embodiment as a variation of the foregoing figures in which a plurality of tubes has been provided for the outside and inside washing of the dental pieces.

Like numerals represent like or similar parts throughout the several figures of the drawings.

DESCRIPTION OF THE PREFERRED EMBODIMENTS

Figure 1:
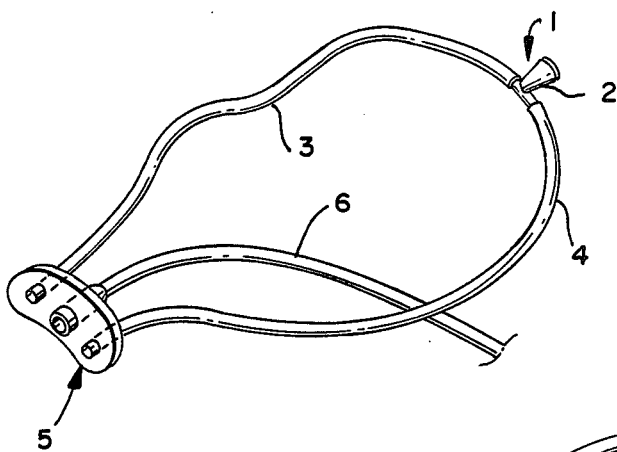
FIG. 1 shows a perspective view of a first embodiment of the hygienizing device of the present invention.
Figure 2:
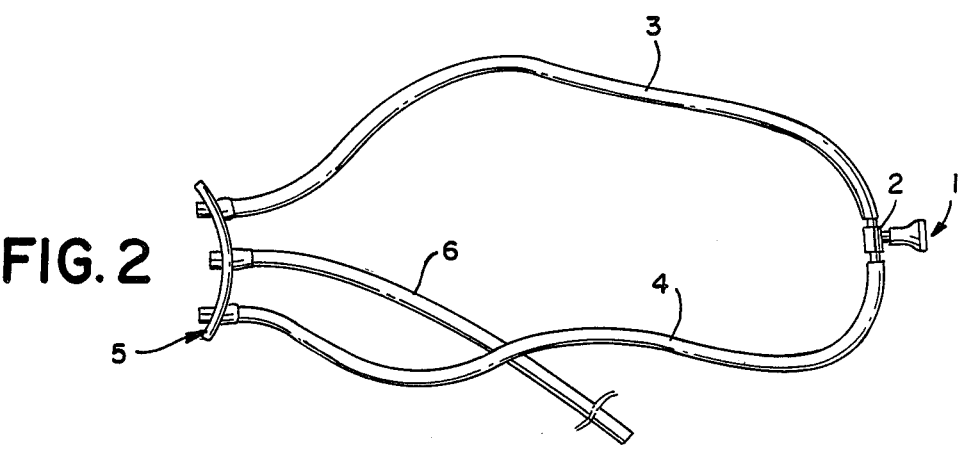
FIG. 2 is a plan view of the device shown in FIG. 1.

In accordance with FIGS. 1 and 2 of the drawings, the device of the present invention, in its first embodiment, comprises basically a nozzle (1) connected to one of the branches of a tubular "T" coupling (2) which is connected to corresponding ducts (3) and (4) intended to provide a current of water between the jaws of the patient.

Nozzles connected at the ends of conduits (3) and (4) are anchored in opposite sides of a bucal adaptor consisting of a plate (5), generally of flexible material, which is readily adaptable so as not to damage the user's mouth.

Plate (5) in turn forms integral part of a drain duct (6) the diameter of which is slightly greater than that of conduits (3) and (4). As shown in said figures, the inlets project above the surface of the plate (5). The drainage duct (6) debouches into a basin (p) as indicated in FIG. 4.

Figure 3:
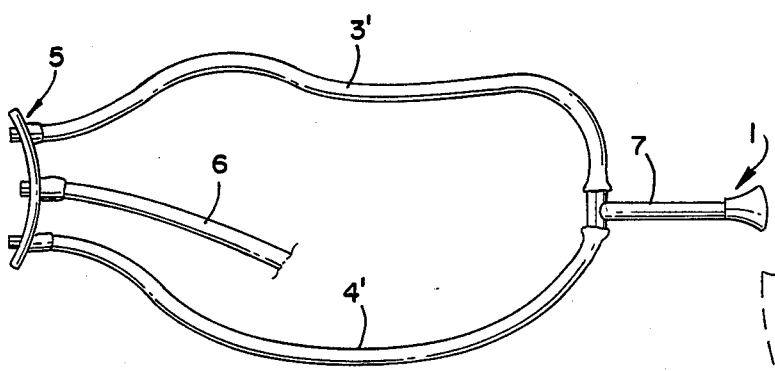
FIG. 3 illustrates a plan view of a second embodiment of the invention.

FIG. 3 shows a second variant of the device according to the invention. Some includes a "T" coupling and, in same, a tube the length of which permits its connection to the selected source by means of a nozzle (1). The "T" coupling is connected to the pair of tubes (3') and (4') which, as in the previous embodiment, are affixed to a plate (5) having a drain tube (6).

Figure 4:
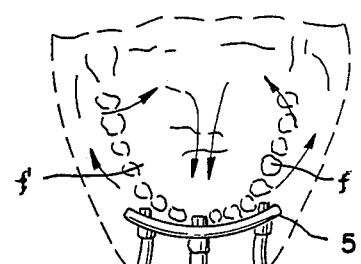
FIG. 4 represents a diagrammatic view of the device applied to the bucal cavity. In this plan view it is possible to visualize the flow of liquid in the interior of the mouth.
Figure 4:
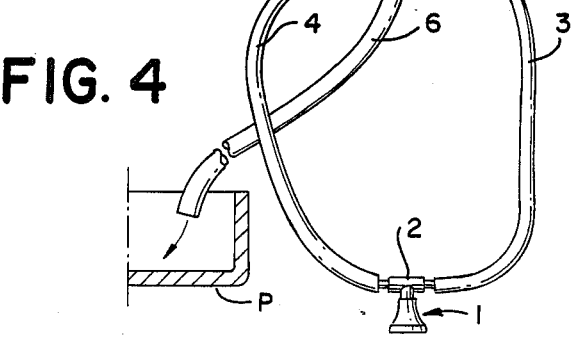

In FIG. 4 the manner of applying the device to the user's mouth can be seen, arrows (f) and (f') indicating the flow of liquid entering through each of ducts (3) and (4). This flow of liquid, acting against the walls of the bucal cavity, return and become joined for drainage through tube (6), after having passed through the interdental spaces and removing the bacterial plaque after eventually carrying off the food residues that may be present.

FIG. 5 represents a third variant of the device. In same, the latter is directly connected to the outlet of a liquid supply source. This embodiment is of convenient use in consulting rooms.

FIG. 6 shows a fourth embodiment of the invention. In same, conduit (3) of the device comprises a parallel small-size receptacle (8) containing a disinfecting or medicinal solution which, through a drip conduit (9) and a regulating valve (10) is communicated with duct (3) in such a manner that the aforesaid solution is carried by the liquid towards the bucal cavity.

FIGS. 7 and 8 show a fifth modification of the invention, in which the bucal adaptor, indicated by reference (5'), is hollow and of flexible material to follow the contour of the dental arcades. The adaptor (5') limiting a chamber (11), is connected to a single water inlet tube (12).

Drainage duct or tube -6- passes through chamber -11-. The inlet of said duct -6- projects beyond the inner wall -13- of adaptor -5'-. Said wall -13- is provided with a plurality of openings -14- the diameter of which can be varied as likewise their number, in order to vary the power of the jets directed against the dental pieces.

Adaptor -5'- extends between the left and right molar vestibulary sectors and in this manner an excellent distribution of the water current in the bucal cavity is obtained.

FIG. 9 shows a sixth variant of the device. In same, the bucal adaptor -5"- comprises two hollow parts -15- and -16- defining respective chambers -15'-16'-.

Piece -15- is connected to the water supply tube -12- and the drain duct -6- passes therethrough. The water outlet of said drain duct -6- is located in space -17- separating both pieces -15- and -16-. The latter are connected together by ducts -18- and the mutually confronting walls -19- and -19'- of both pieces -15- -16- comprise a plurality of openings -20-20'- directed towards opposing faces of the dental arcades, located in said space -17- to retain the adaptor -5"-.

The object of this embodiment is to irrigate the inside outer faces (vestibulary palatine and lingual) by using a double supply of water jets.

FIGS. 10 and 11 represents a seventh embodiment of the invention. In same the device comprises an adaptor -5- with a drainage tube -6- and a water access duct or tube -21- consisting of a tubular section -21'- which is connected on one side to the source of supply and on the other side to a receptacle -22- including covers, of variable shape and size, communicating with a pair of tubes -21"- of smaller diameter that the tubular section -21'- and passing through the adaptor -5- to be located at opposite sides of the bucal cavity. Receptacle -22- is intended to dosify the washwith chemical coagents to complete the treatment and may include liquid or solid chemical compounds. These compounds, if solid, must be water-soluble as likewise the salts, gels, etc. Such substances, including abrasives etc., may be entrained by the liquid current to be supplied through the tubes -21"'- the diameters of which may be varied to increase the power of shock force of the jets.

FIGS. 12 and 13 show a variation of the latter embodiment the difference residing in the provision of a plurality of small-diameter tubes -21-, conveniently distributed to effect a complete washing and permit a better distribution of the currents inside the bucal cavity. In this embodiment tubes -21"- must be situated at opposite sides of the bucal cavity and inside the bucal arcades in order to diversify the directions of the currents exteriorly and interiorly with regard to said arcades.

It is necessary to point out that the device, during the teeth-washing operation, permits a continuous flow of water to be maintained in the mouth, beginning with the left and right sectors thereof, and covering the entire oral cavity, it being possible to modify this current by moving the cheeks or using the tongue, the latter furthermore being used to regulate the outflow of water on being applied against the end of tube -6-, which must be held between the teeth.

These changes in direction and velocity of the water current as consequence of the muscular movements of the patient, enable more effective action being applied against the bacterial plaque and removing superficial deposits.

As has been pointed out in the present specification, although the bacterial plaque is not totally removed its maturing is interfered with, thus preventing that the bacterial deposits reach the pathological level detrimental to bucal tissues.

The invention as set forth may be clearly understood and further explanations will not be required by those versed in the art.

It is obvious that sundry changes as to construction and detail may be made without thereby departing from the scope of the present invention as clearly determined in the following claims.

What I claim is:

1. A device for cleaning a human mouth comprising an elongated plate adapted to be placed between lips and dental arches of the mouth, said plate being made of flexible material and thereby be adapted to conform to the mouth, said plate having three spaced openings, first and second of said openings having equal diameters and a third of said openings having a diameter larger than said first and second openings, water inlet means adapted to receive water from a water supply, a pair of spaced conduits having equal diameters and each having one end connected to said water inlet means and having an opposite end extending through a respective one of the first and second openings in said plate, a third conduit having a larger diameter than said spaced conduits and having one end leading to a drain and having an opposite end extending through the third of said openings for receiving water from the mouth in a continuous washing thereof, a projecting end on the opposite end of said third conduit spaced from said plate thereby being adapted for selective use of the tongue to close the drain conduit.

2. A device as claimed in claim 1 wherein the opposite ends of said spaced conduits are spaced from and on opposite sides of the projecting end on the drain conduit, and said opposite ends of said spaced conduits are directed away from the projecting end on the drain conduit whereby water is directed towards opposite lateral sectors of the mouth.

3. A device as claimed in claim 2, wherein a receptacle having a medicinal solution therein is disposed adjacent one of said spaced conduits and a drip tube establishing communication with said one conduit for delivering the medicinal solution to said one conduit.

4. A device as claimed in claim 2, wherein said water inlet means includes a receptacle having an inlet opening for receiving water and a pair of spaced outlets defining connections for each of said one ends of said pair of spaced conduits.

5. A device as claimed in claim 4 wherein said receptacle includes a removable cover whereby a medicine may be placed in the receptacle for mixing with the water flowing therethrough.

* * * * *